| United States Patent [19] | [11] Patent Number: 5,021,564 |
|---|---|
| Wirth | [45] Date of Patent: Jun. 4, 1991 |

[54] PROCESS FOR PREPARING CEFTAZIDIME PENTAHYDRATE

[75] Inventor: David D. Wirth, Lafayette, Ind.

[73] Assignee: Eli Lilly and Company, Indianapolis, Ind.

[21] Appl. No.: 618,004

[22] Filed: Nov. 26, 1990

Related U.S. Application Data

[63] Continuation of Ser. No. 518,277, May 1, 1990, abandoned, which is a continuation of Ser. No. 407,512, Sep. 14, 1989, abandoned, which is a continuation of Ser. No. 10,252, Feb. 2, 1987, abandoned.

[51] Int. Cl.$^5$ ............................................. C07D 501/38
[52] U.S. Cl. ..................................... 540/225; 540/222
[58] Field of Search .......................................... 540/225

[56] References Cited

U.S. PATENT DOCUMENTS

| 4,258,041 | 3/1981 | O'Callaghan et al. | 424/246 |
|---|---|---|---|
| 4,329,453 | 5/1982 | Brodie et al. | 544/25 |
| 4,537,959 | 8/1985 | Chou | 544/25 |
| 4,616,080 | 10/1986 | Chou | 540/225 |

OTHER PUBLICATIONS

Glaxo Group Ltd., Derwent Abstract No. 85-321449/38 of German Patent No. 3,508,572-A, issued Mar. 8, 1985.

*Primary Examiner*—Nicholas S. Rizzo
*Attorney, Agent, or Firm*—James J. Sales; Leroy Whitaker

[57] ABSTRACT

An improvement in the process of preparing ceftazidime pentahydrate from ceftazidime dihydrobromide which comprises commingling a secondary-amine-type ion-exchange resin such as Amberlite LA-2 in a water-immiscible organic solvent with an aqueous solution of the dihydrobromide, stirring the mixture while maintaining a pH at or below about 6.0 and isolating ceftazidime pentahydrate from the aqueous layer. This process provides significantly higher yields of the pentahydrate than previously could be obtained from the dihydrobromide.

12 Claims, No Drawings

PROCESS FOR PREPARING CEFTAZIDIME PENTAHYDRATE

This application is a continuation of application Ser. No. 518,277, filed May 1, 1990, now abandoned, which is a continuation application of Ser. No. 407,512, filed Sept. 14, 1989, now abandoned, which is a continuation of application Ser. No. 010,252, filed Feb. 2, 1987, now abandoned.

SUMMARY OF THE INVENTION

This invention provides an improvement in the process of preparing ceftazidime pentahydrate from ceftazidime dihydrobromide. The improvement comprises commingling a secondary-amine-type ion-exchange resin such as Amberlite LA-2 in a water-immiscible organic solvent such as dichloromethane with an aqueous solution of ceftazidime dihydrobromide and stirring the resulting mixture while maintaining a pH at or below about 6.0. Ceftazidime can then be isolated from the aqueous layer as the pentahydrate by standard procedures.

The advantage of this improved process is that it provides much higher yields of ceftazidime pentahydrate than previously could be obtained from ceftazidime dihydrobromide.

DETAILED DESCRIPTION

This invention relates to an improvement in the process for preparing the cephalosporin antibiotic known as ceftazidime. In particular, it relates to an improvement in the process for preparing the pentahydrate form of ceftazidime from the dihydrobromide form of ceftazidime.

The commercially successful, semi-synthetic cephalosporin antibiotic ceftazidime is also chemically named 1-[[7-[[(2-amino-4-thiazol-yl) [1-carboxy-1-methylethoxy)imino]acetyl]amino]-2-carboxy-8-oxo-5-thia-1-azabicyclo[4.2.0]oct-2-ene-3-yl]methyl]pyridinium hydroxide inner salt or (6R,7R)-7-[(Z)-2-(2-aminothiazol-4-yl)-2-(2-carboxyprop-2-oxyimino)acetamido]-3-(1-pyridiniummethyl)ceph-3-em-4-carboxylate (see, for example, U.S. Pat. No. 4,258,041).

An especially useful pharmaceutical form of ceftazidime is its pentahydrate form. Ceftazidime pentahydrate is described in U.S. Pat. No. 4,329,453.

The preparation of semi-synthetic cephalosporin antibiotics such as ceftazidime in advantageous forms such as the pentahydrate generally involves several steps. Because product losses usually occur at each step, multistep processes are expensive. Improvements in such processes which increase product yield are, therefore, of great value.

This invention provides an improvement in the yield of ceftazidime pentahydrate when obtaining it from ceftazidime dihydrobromide. The improvement comprises using a secondary-amine-type ion-exchange resin to remove undesirable by-products such as bromide ions from the aqueous solution of ceftazidime after dissolution of the dihydrobromide, thereby allowing ceftazidime pentahydrate to be isolated in much higher yield. The process of this invention provides an improvement in yield whether or not a polystyrene resin treatment is also used. Yield improvements in the range of up to 25% have been observed.

Secondary-amine-type ion-exchange resins such as Amberlite LA-2 have been used in the purification of cephalosporins, including ceftazidime (see, for example, U.S. Pat. No. 4,258,041, Examples 8 and 12) and ceftazidime bishydrochloride (see U.S. Pat. No. 4,329,453, Example 1). In such instances, however, the resins either were used in a different way, i.e., bromide ion removal was not involved, or showed no advantage over similar isolation methods. For example, the yields obtained using the procedures of Examples 1, 2, 3 and 4 in U.S. Pat. No. 4,329,453 were about the same.

Secondary-amine-type ion-exchange resins which are suitable for the process of this invention are liquid and have a high molecular weight. Such resins are oil soluble, but water insoluble. Preferably, the resin will have a molecular weight in the range of 350–400 and a capacity of approximately 2.5–2.8 meq/g (2.1–2.3 meq/mL). Examples of resins which can be used are Amberlites LA-1 and LA-2 (Rohm & Haas, Philadelphia, PA 19105).

The ceftazidime dihydrobromide used in the process of this invention may be either the dihydrobromide itself or the dihydrobromide in a hydrated form such as the dihydrobromide monohydrate or dihydrate.

In carrying out the process of this invention, a solution of the ion-exchange resin in a suitable solvent is commingled with an aqueous solution of the ceftazidime dihydrobromide, preferably by adding the resin to the solution of the antibiotic. The solvent in which the ion-exchange resin is presented can be selected from a number of water-immiscible organic solvents. Examples of suitable solvents are dichloromethane, chloroform, ethyl acetate and methyl ethyl ketone. A preferred solvent is dichloromethane.

When the ion-exchange resin is mixed with the aqueous ceftazidime dihydrobromide solution, the resin will raise the pH of the solution. Care should be taken to maintain the pH of the resulting solution at or below about 6.0 by adding appropriate amounts of acid or base. Phosphoric acid is a particularly suitable acid for lowering the pH.

After the resin is added, the resulting mixture should be stirred to permit adsorption of by-products and bromide ions by the resin. The length of time the mixture is stirred is not critical and will vary, depending on the volume of the solution and the amount of resin used. In general, the mixture should be stirred for at least from about 1 to about 20 minutes.

For best results from this process, the aqueous ceftazidime solutions should be chilled. A preferred temperature range is from about 5° to about 15° C. A range of from about 8° to about 12° C. is especially preferred.

Following the use of the liquid ion exchange resin, the ceftazidime can be recovered in its pentahydrate form from the aqueous layer by standard procedures, such as those described in U.S. Pat. No. 4,329,453.

The following examples further illustrate the process of this invention.

EXAMPLE 1

Preparation of Ceftazidime Pentahydrate from Ceftazidime Dihydrobromide a. Prior Ceftazidime Pentahydrate Process Ceftazidime dihydrobromide (potency 70.6%, 21.26 g) was added to deionized water (30 mL) which had been prechilled to 10° C. Sodium hydroxide (4M) was added dropwise to raise the pH to 2.1 at 10° C. The solution was stirred 20 min at 10° C. and filtered across a pad of filter aid. The pad was rinsed with water (10 mL), and the aqueous solutions were combined.

The pH of the combined solution was raised to 6.0 with 4M sodium hydroxide, and the resulting solution was eluted across Dianion HP-20 resin (45 mL) which had been prechilled to ca. 10° C. The total volume collected from the resin, including the rinse of dionized water, was 120 mL.

Crystallization was induced by adjusting the pH to 4.0 with 4M phosphoric acid and adding seed crystals. After 1½ hr, more phosphoric acid was added over a 2-hr period to achieve a pH of 3.7. The pH was kept at 3.7 and the temperature was lowered to 0°–5° C. for 1 hr while the product crystallized. The product was collected by filtration, rinsed with cold water and cold acetone, and dried in vacuo at ambient temperature. This procedure gave 11.94 g of ceftazidime pentahydrate. The assay was 84.4%, and the corrected yield was 67.2%. A typical amount lost in the mother liquor by this procedure is 21%.

b. Improved Ceftazidime Pentahydrate Process

Ceftazidime dihydrobromide (70.6% potency, 21.26 g) was added to deionized water (30 mL) which had been chilled to 10° C. Sodium hydroxide (4M) was added dropwise to raise the pH to 2.0 at 10° C. The slurry was stirred at 10° C. for 20 to 30 min to insure complete dissolution and then filtered across a small pad of filter aid. The pad was rinsed with deionized water (10 to 15 mL). The aqueous solutions were combined and chilled to 5° C.

Amberlite LA-2 (30 mL) was diluted with dichloromethane (120 mL) and washed sequentially with 0.4M sodium hydroxide (150 mL) and a 3% aqueous solution of sodium chloride (150 mL). The resulting solution was added over a 5 min period to the ceftazidime solution, keeping the temperature at or below 12° C. The pH was prevented from rising above 6.0 by the addition of 85% phosphoric acid (0.5 mL).

After this mixture was stirred for 2 min at 10° C. and pH 5.9, the layers were separated. The aqueous solution was washed with dichloromethane (140 mL) and then evaporated under vacuum to remove residual dichloromethane, giving a clear pale-yellow solution. This solution was then eluted across a column of Dianion HP-20 (40 mL) which had been prewashed with ice-cold deionized water (100 mL). The HP-20 column was rinsed with water (20 mL) which had been used to back-extract the combined dichloromethane solutions. The total column eluant collected was 120 mL.

The pH of the ceftazidime solution was lowered to 4.5 with 4M phosphoric acid, and the solution was seeded. The solution was stirred for 2½ hr at 0-5° C., during which the pH had risen to 4.7 and a large amount of crystals had formed. Phosphoric acid (4M) was then added dropwise over a 1 hr period to achieve a pH of 3.7. More acid was added dropwise over the next ½ hr to maintain this pH. After the pH was stabilized, the slurry was stirred slowly in an ice bath for 1 hr. The crystals were filtered and washed twice with cold deionized water (2×30 mL) and then with cold acetone (30 mL). The product was dried overnight at ambient temperature at a pressure of about 80 mm Hg. This procedure gave 13.57 g of ceftazidime pentahydrate. The assay was 85.4%, and the corrected yield was 77.3%. Another 11.1% yield was obtained from the combined mother liquors and washes.

EXAMPLE 2

Alternate Preparation of Ceftazidime Pentahydrate from Ceftazidime Dihydrobromide The improved process of Example 1 was repeated except that Dianion HP-20 resin was not used. The aqueous ceftazidime solution obtained after the evaporation step was crystallized immediately by lowering the pH of the solution to 4.6 and proceeding as described in Example 1.

This procedure gave 15.92 g of ceftazidime pentahydrate. The assay was 84.4%, and the corrected yield was thus 89.6%. Another 7.7% yield was present in the mother liquor.

I claim:

1. In the process for preparing ceftazidime pentahydrate from ceftazidime dihydrobromide, the improvement which comprises adding a secondary-amine-type ion-exchange resin in a water-immiscible organic solvent to an aqueous solution of ceftazidime dihydrobromide, stirring the resulting mixture while maintaining a pH at or below about 6.0 until the byproducts are adsorbed on the resin and isolating the ceftazidime in its pentahydrate form from the aqueous phase.

2. A process of claim 1 wherein the ion-exchange resin is Amberlite LA-2.

3. A process of claim 1 wherein the ion-exchange resin is Amberlite LA-1.

4. A process of claim 1 wherein the water-immiscible solvent is dichloromethane.

5. A process of claim 2 wherein the water-immiscible solvent is dichloromethane.

6. A process of claim 3 wherein the water-immiscible solvent is dichloromethane.

7. A process of claim 1 wherein the aqueous solution of ceftazidime dihydrobromide is chilled to a temperature of from about 5° to about 15° C.

8. A process of claim 2 wherein the aqueous solution of ceftazidime dihydrobromide is chilled to a temperature of from about 5° to about 15° C.

9. A process of claim 6 wherein the aqueous solution of ceftazidime dihydrobromide is chilled to a temperature of from about 5° to about 15° C.

10. A process for preparing ceftazidime pentahydrate using ceftazidime dihydrobromide comprising:
    filtering an aqueous solution of ceftazidime dihydrobromide having a pH of about 2.0,
    mixing a secondary-amine-type ion-exchange resin in a water-immiscible organic solvent with the filtered aqueous solution of ceftazidime dihydrobromide while maintaining a pH at or below about 6.0 until the byproducts are absorbed from the mixture onto the resin; and
    crystallizing ceftazidime pentahydrate by seeding at least a portion of the mixture, said mixture having a pH of about 4.5 when seeded.

11. The process of claim 10 wherein the ion-exchange resin is Amberlite LA-2 or Amberlite LA-1.

12. The process as recited in claim 10 wherein said steps are accomplished at a temperature of from about 5° to about 15° C.

* * * * *